United States Patent [19]
Quinn

[11] Patent Number: 5,206,706
[45] Date of Patent: Apr. 27, 1993

[54] ALIGNMENT OF AN ELLIPSOMETER OR OTHER OPTICAL INSTRUMENT USING A DIFFRACTION GRATING

[75] Inventor: William E. Quinn, Middlesex Boro, N.J.

[73] Assignee: Bell Communications Research, Inc., Livingston, N.J.

[21] Appl. No.: 723,580

[22] Filed: Jul. 1, 1991

[51] Int. Cl.$^5$ .......................... G01B 11/00; G01J 4/00
[52] U.S. Cl. .................................. 356/400; 356/369; 356/154
[58] Field of Search ...................... 356/138, 153–154, 356/399–407, 363, 356, 354, 369

[56] References Cited
FOREIGN PATENT DOCUMENTS 0023902 2/1986 Japan .................................. 356/363
8504266 9/1985 World Int. Prop. O. .......... 356/363

Primary Examiner—F. L. Evans
Assistant Examiner—K. P. Hantis
Attorney, Agent, or Firm—Leonard Charles Suchyta; Charles S. Guenzer

[57] ABSTRACT

Alignment method and procedure for accurately determining the off-normal angle of incidence of an optical beam with a sample, for example, in ellipsometry. A diffraction grating is fabricated with a grating period chosen such that, when a laser beam irradiates the grating placed at the sample area, a beam is diffracted generally along the incoming laser beam. The laser is then angularly moved with respect to the grating until the two beams are auto-collimated, i.e., made coincident. The angle of incidence is then accurately determined from the laser wavelength and the grating period through well known equations.

9 Claims, 3 Drawing Sheets

ALIGNMENT OF AN ELLIPSOMETER OR OTHER OPTICAL INSTRUMENT USING A DIFFRACTION GRATING

FIELD OF THE INVENTION

The invention relates generally to optical measuring devices, such as ellipsometers. In particular, the invention relates to the optical alignment of such devices.

BACKGROUND ART

Aspnes and the present inventor disclosed an ellipsometer in U.S. Pat. No. 5,091,320, and incorporated herein by reference. This highly sensitive ellipsometer allows the characterization of the composition of a semiconductive thin film as it is being grown in a closed deposition chamber. As illustrated in the schematic illustration of FIG. 1, the thin film is grown on a substrate 10, usually a semiconductor wafer, held on a substrate holder 12 located inside the enclosed growth chamber. If the growth process is molecular beam epitaxy (MBE) or organo-metallic molecular beam epitaxy (OMMBE), the growth chamber is a vacuum chamber 14 held at fractions of a torr. Two viewing ports 16 and 18 are disposed at about 70° on either side of the surface normal 20 of the substrate holder 12. Low-strain optical windows 22 in the viewing ports 16 and 18 provide optical access to the growing thin film. A viewing port 24 with its own window is usually located on the surface normal 20. The ellipsometer of Aspnes and Quinn includes a light source 26 outputting a beam along an incident axis 28, an entrance iris 30, a rotatable input polarizer 32, a rotatable output polarizer 34 and an exit iris 35 disposed on a reflection axis 36, and an optical detector 38. A computer 40 receives the measured optical intensities and controls the polarizers 32 and 34. They chose to use a wide band Xe arc lamp as the light source 26 and include a monochromator just before the optical detector 38. More details may be found in their patent. The ellipsometer provides an incident beam of a predetermined polarization state extending through the window of the input port 22 and striking the substrate 10 at an oblique angle $\phi_i$ away from the surface normal. The incident radiation interacts with the top micrometer or so of material on the substrate 10 (i.e., the growing thin film) and is reflected in a changed polarization state along the reflection axis 36 extending through the output port 18. The reflection axis 36 is angularly displaced from the normal 20 by $\phi_0$. For specular reflection, $$\phi_i = \phi_0. \tag{1}$$

The ellipsometer of Aspnes and Quinn has been used to control the growth of thin films of ternary semiconductors, e.g. $Al_xGa_{1-x}As$. It is highly precise, capable of controlling variations of the alloying percentage x to less than 0.1%

However, its accuracy has been substantially less. Accuracy depends on the absolute value of the alloying percentage x, not just its variation. The accuracy has been limited by the lack an exact numerical value of the incident angle $\phi_i$, which is used in reducing the experimentally derived ellipsometric data to the complex refractive indices or dielectric functions of the material being probed by the ellipsometer. In the past, the incident angle $\phi_i$ was determined by triangulation. However, the sample holder 12 is within the vacuum chamber 14 having very limited optical access, and its angular position cannot usually be moved. As a result, triangulation becomes difficult. Another commonly used technique involves auto-collimation in which the sample is replaced by a mirror mounted on a precision rotatable stage. The stage or light source is then moved until the reflected beam coincides with the incident beam. Thereafter, the stage is rotated through a precisely measured angle to its operational position. Reflective auto-collimation is not useful with growth chambers because the substrate holder is designed for considerations inconsistent with a precision rotatable stage. Another indirect technique involves mounting a reference sample of known refractive indices and performing ellipsometry upon it. The value of $\phi_i$ which best reduces the ellipsometric data to the known (or assumed) dielectric function of the sample is taken as the incident angle. However, this technique requires that the actual surface composition of the reference sample be precisely known and be constant. Therefore, the accuracy of the indirect approach depends on the unknown reproducibility of the reference sample.

SUMMARY OF THE INVENTION

Accordingly, an object of the invention is to provide a highly accurate angular alignment of a sample relative to an optical beam.

Another object of the invention is to provide an accurate value of the angular displacement between an optical beam incident on a sample and the surface normal of that sample.

The invention can be summarized as the method and apparatus required to determine the oblique angle of incidence of an optical beam on a sample. A diffraction grating is placed in the position of the sample. Its period is selected such that, when an optical beam of narrow frequency width, e.g. a laser beam, shines on the grating, a non-zero-order diffraction beam can be made coincident with the laser beam. When the beams are coincident, the angle of incidence is related by well known equations to the grating period and the optical frequency.

DETAILED DESCRIPTION OF THE PREFERRED EMBODIMENT

Figure 1:
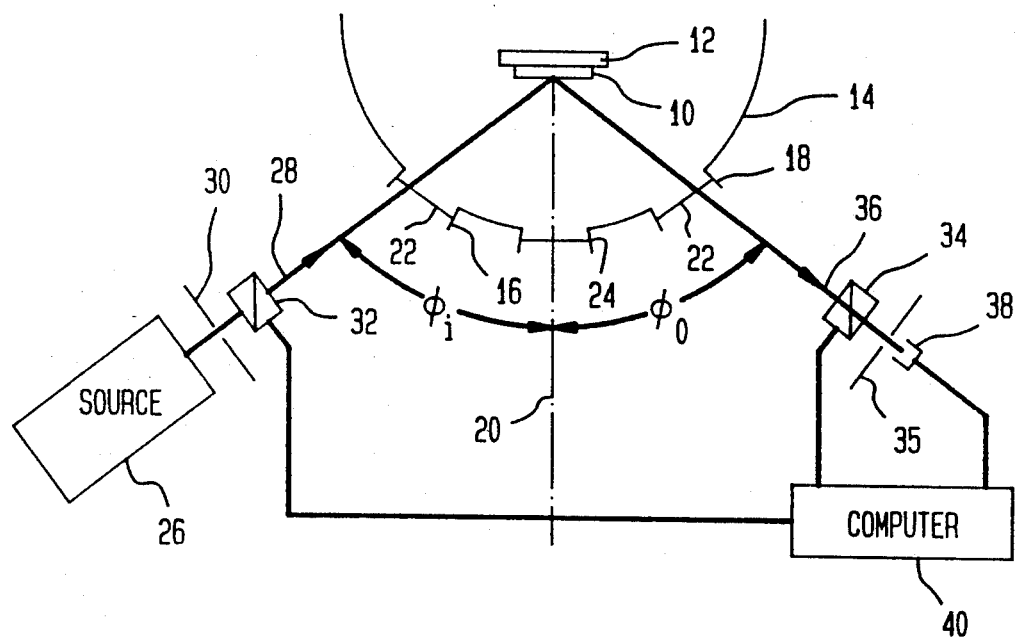
FIG. 1 is a schematic illustration of the geometry involved in ellipsometric monitoring of a growing thin film.
Figure 2:
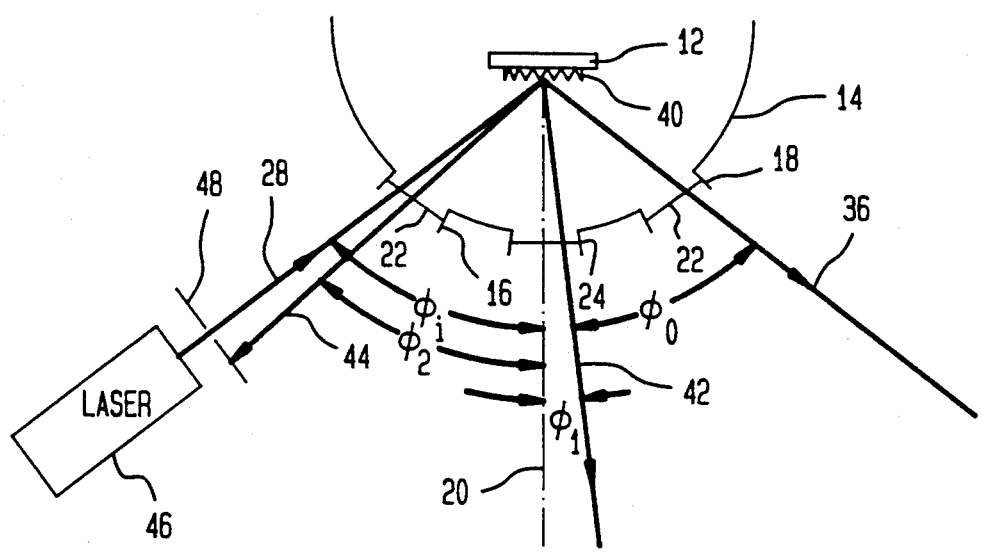
FIG. 2 is a schematic illustration of the method of measuring the incident angle of an optical beam.

According to the invention, auto-collimation of a higher-order beam diffracted from a grating positions the input beam at a precisely fixed angle relative to the normal of the grating. As illustrated in FIG. 2, a diffraction grating 40 having a grating period d replaces the substrate 10 on the substrate holder 12. The input beam propagating light of wavelength λ along the incident axis 28 is both specularly reflected in a zero-order beam along the reflection axis 36 and diffracted into multiple higher-order beams. The figure illustrates a first-order beam 42 located at an angle $\phi_1$ from the normal 20 and a second-order beam 44 at an angle $\phi_2$. The angles are interrelated by well known equations:

$$d \sin \phi_i - d \sin \phi_1 = \lambda \tag{2}$$

and $$d \sin \phi_i + d \sin \phi_2 = 2\lambda. \tag{3}$$

If the second-order beam 44 is auto-collimated with the input beam 28, that is, the two beams 28 and 44 are made coincident, then $$\phi_2 = \phi_i. \tag{4}$$

Substitution of Equation (4) into Equation (3) and rearranging it produce a calculable value of the incident angle $$\phi_i = \sin^{-1} \frac{\lambda}{d} \tag{5}$$

Therefore, under the auto-collimation condition, the incident angle $\phi_i$ can be calculated from the grating period d and the light wavelength $\lambda$. Alternatively, if the grating is designed according to a particular value of $\phi_i$, when the diffracted beam is auto-collimated with the incident beam, the angular relationship between the grating and the incident beam accurately conforms to this value of the incident angle. For auto-collimation of the second-order beam 44, $\phi_1 = 0$ so that the first-order beam 42 is coincident with the normal 20.

EXAMPLE

The invention was demonstrated using a HeNe laser 46 during the alignment procedure. The laser 46 emits at $\lambda = 632.82$ nm. With this value of $\lambda$ and the nominal value of 70° for $\phi_i$, Equation (5) required that the grating 40 have a non-standard pitch 1/d of 1484.9 grooves per millimeter.

Figure 3:
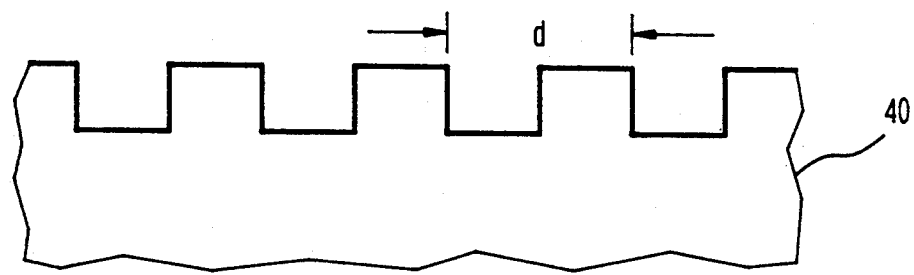
FIG. 3 is a cross-sectional view of a diffraction grating usable with the invention.

Such a grating was custom made. Polymethylmethacrylate (PMMA) was coated as a resist layer on a two-inch (5 cm) GaAs wafer. An electron beam wrote the grating pattern of nominal period d into a 2 mm square of the resist at the center of the wafer, the resist was developed, and then the GaAs was etched with reactive ion etching with $BCl_3$ to transfer the grating pattern to the substrate. There resulted a grating 40, as illustrated in cross-section in FIG. 3, of period d. The grooves were approximately 200 nm deep. The groove width approximately equaled the mesa width. After its fabrication, the grating was mounted on an indium-free (clipping) mounting block. It was determined that mounting with In could warp the 500 $\mu$m thick substrate. The grating period d was measured outside of the chamber 14 after the grating has been attached to the mounting block using the HeNe alignment laser 46 and a transit. Its value was 672.0 nm, which would determine the true value of $\phi_i$ in the alignment procedure. A silicon diffraction grating would have been preferred. Blazing would have increased the intensity of the desired diffraction order.

The mount holding the diffraction grating 40 was then attached to the substrate holder 12. A pencil tip punched a 1 mm hole in a paper card 48. The card 48 was then taped to the laser 46 such that the laser beam 28 penetrated the hole. The laser 46 was then substituted for the light source 26 in the ellipsometer set up around the vacuum chamber 14. Rough alignment of the laser beam 28 with the small area of the grating 40 was achieved by projecting the first-order beam 38 onto another white card and maximizing its intensity. The second-order beam 44 was then observed on the unperforated portion of the paper card 48. The laser 46 and the attached card 48 were moved laterally until the second-order beam 44 disappeared into the punched hole, in which situation the second-order beam 44 was auto-collimated with the laser beam 28, and the incident angle $\phi_i$ was precisely determined from the values of d and $\lambda$. The entrance and exit irises 30 and 35 were then centered on the incident and specularly reflected beams 28 and 36 to lock in the alignment when using the Xe arc lamp and sample being tested by the ellipsometer.

Figure 4:
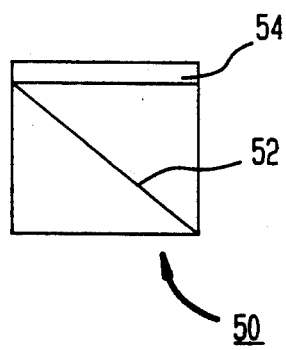
FIG. 4 is a cross-sectional view of a beam splitter usable in auto-collimation.

The accuracy in the value of $\phi_i$ using the above technique is estimated to be about $\pm 0.06°$. The accuracy could be improved using more elaborate techniques. For example, a beam splitter 50, illustrated in cross-section in FIG. 4, could be used to intercept the input beam 28 and the second-order beam 44. The beam splitter 50 is a cube of quartz having a half-silvered diagonal 52. Additionally, one side is coated with a reflector 54. The laser light shining from the left side is partially transmitted across and partially reflected downwardly from the interface 52. The second-order beam propagating from the right is partially reflected upwardly from the interface 52, reflected downwardly by the reflector 54, and partially transmitted downwardly through the interface 52. The optical pattern at the bottom of the beam splitter 50 is monitored. In auto-collimation, the laser beam and the second-order beam merge into a single beam.

Although the above embodiment uses the second-order diffracted beam for auto-collimation, any higher-order (greater than zero order) diffracted beam could be auto-collimated with the incident beam. Equation (5) can be generalized to $$\phi_i = \sin^{-1} \frac{n \cdot \lambda}{2d}, \tag{6}$$

where n is a positive integer.

The choice of a nominal incident angle $\phi_i$ of 70° was dictated by the existing viewing ports 16 and 18. Many vacuum stations are configured with two viewing ports separated by 135° so that $\phi_i$ would be 67½°. Ellipsometry is most accurate when performed near the pseudo-Brewster angle, that is, when the tangent of incident angle $\phi_i$ equals the refractive index of the material being probed. For most semiconductive materials, this is about 70°-75°. Sensitivity considerations suggest limiting $\phi_i$ to the range of 60° to 75°, preferably 65° to 75°.

Although the above example used a laser as a light source for the alignment, a narrow-bandwidth light source could be substituted, e.g., a Xe lamp with a monochromator. The bandwidth needs to be small enough that the spectrally induced beam spreading in the diffracted beam is less than the desired angular accuracy.

The alignment method and apparatus of the invention thus provide a simple but highly accurate alignment of an ellipsometer. The accuracy allows the ellipsometer to provide accurate absolute values of material compositions. The invention can be used for other optical measuring equipment in which the off-normal angle of incidence needs to be accurately known.

What is claimed is:

1. A method of aligning an optical instrument, comprising the steps of:
   irradiating along a first axis a diffraction grating having a grating period of d with an incident beam of light having a wavelength λ, thereby diffracting along a second axis at least an n-th order diffracted beam from said grating, n being an integer greater than zero; and
   auto-collimating said n-th order diffracted beam with said incident beam, wherein said first and second axis are made to be substantially coincident, whereby an angular orientation between said incident beam and said grating is established, thereby determining an angle of incidence between said incident beam and said grating at said established orientation.

2. A method as recited in claim 1, wherein n is equal to 2.

3. A method as recited in claim 2, wherein said irradiating step includes observing a first-order diffracted beam while moving said incident beam.

4. A method as recited in claim 1, wherein said auto-collimating step comprises the steps of:
   observing a separation between said incident beam and said n-th order diffracted beam; and
   changing said angular orientation until said separation disappears.

5. A method as recited in claim 1, further comprising the step of placing said diffraction grating at a sample area within an ellipsometer before the step of irradiating the diffraction grating.

6. A method as recited in claim 5, further comprising substiting a narrow-bandwidth light source for a light source of said ellipsometer, said narrow-bandwidth light source producing said incident beam.

7. A method as recited in claim 1, wherein said angle of incidence is determined according to the equation $$\phi_i = \sin^{-1} \frac{n \cdot \lambda}{2d}.$$

8. An ellipsometer system, comprising:
   an ellipsometer including an ellipsometric light source for irradiating a sample area with an optical beam at an angle of incidence $\phi_i$; and
   a diffraction grating having a grating period d disposed at said sample area, wherein $$\phi_i = \sin^{-1} \frac{n \cdot \lambda}{2d},$$

wherein n is a positive integer and λ is a wavelength of light emitted by a narrow-bandwidth light source physically substitutable for said light source in said ellipsometer.

9. An ellipsometer system as recited in claim 8, wherein, a laser emitting light at said wavelength λ is said narrow-bandwidth light source.

* * * * *